(12) United States Patent
Wada

(10) Patent No.: US 11,173,279 B2
(45) Date of Patent: Nov. 16, 2021

(54) MICROCATHETER

(71) Applicant: Hidetaka Wada, Shizuoka (JP)

(72) Inventor: Hidetaka Wada, Shizuoka (JP)

( * ) Notice: Subject to any disclaimer, the term of this patent is extended or adjusted under 35 U.S.C. 154(b) by 446 days.

(21) Appl. No.: 16/096,881

(22) PCT Filed: Apr. 24, 2017

(86) PCT No.: PCT/JP2017/016203
§ 371 (c)(1),
(2) Date: Oct. 26, 2018

(87) PCT Pub. No.: WO2017/195580
PCT Pub. Date: Nov. 16, 2017

(65) Prior Publication Data
US 2019/0134348 A1 May 9, 2019

(30) Foreign Application Priority Data

May 10, 2016 (JP) .............................. JP2016-094310

(51) Int. Cl.
*A61M 25/00* (2006.01)
*A61B 1/00* (2006.01)

(52) U.S. Cl.
CPC ..... *A61M 25/0053* (2013.01); *A61B 1/00078* (2013.01); *A61M 25/005* (2013.01);
(Continued)

(58) Field of Classification Search
CPC .......... A61M 25/0053; A61M 25/0054; A61M 25/0012; A61M 25/005; A61M 25/0045; A61M 2025/0042; A61B 1/00078
See application file for complete search history.

(56) References Cited

U.S. PATENT DOCUMENTS 5,976,120 A * 11/1999 Chow ............... A61M 25/0012
604/525
6,171,296 B1 1/2001 Chow
(Continued)

FOREIGN PATENT DOCUMENTS

JP 2001-269411 10/2001
JP 2001269411 A * 10/2001 ............. B29C 48/49
(Continued)

OTHER PUBLICATIONS

International Search Report dated Jun. 13, 2017 from corresponding International PCT Patent Application No. PCT/JP2017/016203, 2 pages.

*Primary Examiner* — Nathan R Price
*Assistant Examiner* — Anh Bui
(74) *Attorney, Agent, or Firm* — Ohlandt, Greeley, Ruggiero & Perle, L.LP.

(57) ABSTRACT

A microcatheter is characterized as having a hardness-transition section along an entire or partial length an outer layer, hardness of the outer layer varying in the hardness-transition section so as to increase from the distal tip to the proximal tip along the lengthwise direction, due to arrangement of a second forming material in a stripe pattern extending in the lengthwise direction of the outer layer in the first forming material including a forming material formable into the outer layer so that a surface area ratio of the two forming materials in a circumferential direction of a cross section varies along the lengthwise direction for the first forming material and the second forming material.

20 Claims, 5 Drawing Sheets

(52) U.S. Cl.
CPC .... *A61M 25/0012* (2013.01); *A61M 25/0045* (2013.01); *A61M 25/0054* (2013.01); *A61M 2025/0042* (2013.01)

(56) References Cited

U.S. PATENT DOCUMENTS

| | | | | |
|---|---|---|---|---|
| 6,355,027 B1 * | 3/2002 | Le | ............ | A61M 25/0054 604/525 |
| 2017/0273566 A1 * | 9/2017 | Van Der Linde | ...... | A61B 34/20 |

FOREIGN PATENT DOCUMENTS

| | | |
|---|---|---|
| JP | 2001-523143 | 11/2001 |
| JP | 2002-541877 | 12/2002 |
| JP | 2003-501160 | 1/2003 |
| JP | 2007-89847 | 4/2007 |
| WO | 98/50097 | 11/1998 |
| WO | 2016/034598 | 3/2016 |

\* cited by examiner

MICROCATHETER

TECHNICAL FIELD

The present disclosure relates to a microcatheter for insertion into a blood vessel.

BACKGROUND ART

A microcatheter for insertion in a narrow blood vessel is conventionally used for treatment or diagnosis of the organs and blood vessels. The microcatheter is inserted into a blood vessel, a tip of the microcatheter is navigated to a site of an organ or a blood vessel for which treatment or diagnosis is required, and a therapeutic agent, contrast agent, or the like is administered or injected. Although reliably navigating the tip of the microcatheter to the target site is difficult due to narrow blood vessels twisting in a complex manner and having numerous branches, operators of many experience levels, not just operators who are extremely experienced, are required to perform reliable navigating of the tip. Thus the microcatheter is conventionally required to have operability.

The "operability" of the microcatheter means properties such as "pushability" as the ability to be pushed in, "torque transmittance" as the ability to be rotated, and "anti-kinking performance" as avoidance of undesirable bending; and various types of microcatheter structures are proposed in order to improve these various types of operability. One means for improving such operability is to make the distal tip side, that is, the tip of the microcatheter, flexible relative to the proximal end side, that is, the operating side, and to improve overall operability at the proximal end side. Patent Literature 1 and Patent Literature 2 are examples of changing hardness in the lengthwise direction of this microcatheter.

The microcatheter of Patent Literature 1 is characterized by: a tip part of a catheter having at least a first region and a second region; an inner layer present over the entire length of the catheter, and a reinforcing layer that covers the inner layer in a region in which at least the first outer layer and the second outer layer are present, as well as a third outer layer in cases in which a third outer layer exists, are braids of strands; the first outer layer is covered by a reinforcing layer in the first region and the second region; the first outer layer is made from a resin material having a Shore hardness less than or equal to 50 D; the first outer layer is covered by the second outer layer in the second region; and the second outer layer includes a region in which resins of at least two types of Shore D hardness continuously transition.

Then by providing the second outer layer with the region in which the resins of at least two types of Shore D hardness continuously transition, a microcatheter is provided that has a continuous stiffness gradient from the tip part to the hand-end part. The second outer layer is formed by melt mixing resin materials, using computer control to continuously vary rotation rate of a gear pump attached to a tip of an extruder, changing outer diameter and resins, and making stiffness vary continuously.

The microcatheter of Patent Literature 2 is characterized in that an outer layer is formed by extrusion molding of a blend or mixture of two materials having mutually different hardness values, and the composition ratio of the two materials is varied during extrusion molding to vary hardness of an integrally-formed tube along the lengthwise direction.

CITATION LIST

Patent Literature

Patent Literature 1: Unexamined Japanese Patent Application Kokai Publication No. 2007-89847
Patent Literature 2: Unexamined Japanese Patent Application Kokai Publication (Translation of PCT Application) No. 2003-501160

SUMMARY OF INVENTION

Technical Problem

However, in the conventional microcatheter, hardness is varied due to varying the mixing ratio of the forming materials, hardness is uniform in the circumferential direction, and thus although prescribed operability is improved, operation while maintaining directionality of the distal tip is difficult.

In consideration of such circumstances, an objective of the present disclosure is to provide a microcatheter that, in addition to having an ability to improve operability, enables transmission of force that differs with position along the circumferential direction rather than the conventional propagation of uniform force, enables operation of the distal tip with good directionality, and further improves operability.

Solution to Problem

A microcatheter of a first aspect includes, in a part or an entire lengthwise direction length of an outer layer, a hardness-transition section is arranged in which hardness of the outer layer varies so as to increase from a distal tip to a proximal tip along the lengthwise direction, due to a second forming material being arranged in a stripe pattern extending in a lengthwise direction of the outer layer in a first forming material including a forming material formable into the outer layer, and a surface area ratio of two forming materials in a circumferential direction of a cross section varying along the lengthwise direction, the two forming materials being the first forming material and the second forming material.

In the microcatheter of a second aspect, the surface area ratio of the two forming materials of the hardness-transition section varies in a stepwise or linear manner along the lengthwise direction.

In the microcatheter of a third aspect, the surface area ratio of the two forming materials varies along the lengthwise direction due to the surface area in the circumferential direction occupied by the second forming material relative to the first forming material of the hardness-transition section varying along the lengthwise direction.

In the microcatheter of a fourth aspect, the second forming material of the hardness-transition section includes three stripes arranged in the circumferential direction, and the surface area ratio of the two forming materials varies along the lengthwise direction due to varying along the lengthwise direction of a surface area in the circumferential direction occupied by the second forming material relative to the first forming material.

In the microcatheter according to a fifth aspect, the surface area ratio of the two forming materials varies along the lengthwise direction due to varying along the lengthwise direction of a surface area in a thickness direction occupied by the second forming material relative to the first forming material of the hardness-transition section.

In the microcatheter according to a sixth aspect, the second forming material of the hardness-transition section includes three stripes arranged in the circumferential direction, and the surface area ratio of the two forming materials varies along the lengthwise direction due to varying along the lengthwise direction of a surface area in the thickness direction occupied by the second forming material relative to the first forming material.

In the microcatheter according to a seventh aspect, the surface area ratio of the two forming materials varies along the lengthwise direction due to varying along the lengthwise direction of a surface area in the circumferential direction and thickness direction occupied by the second forming material relative to the first forming material of the hardness-transition section.

In the microcatheter according to an eighth aspect, the second forming material of the hardness-transition section includes three stripes arranged in the circumferential direction, and the surface area ratio of the two forming materials varies along the lengthwise direction due to varying along the lengthwise direction of a surface area in the circumferential direction and thickness direction occupied by the second forming material relative to the first forming material.

In the microcatheter according to a ninth aspect, among the two forming materials of the hardness-transition section, Shore hardness of one forming material is 20 D to 30 D, and Shore hardness of the other forming material is 65 D to 80 D.

In the microcatheter according to a tenth aspect, hardness values of the two forming materials of the hardness-transition section have a ½-fold to ¼-fold difference.

In the microcatheter according to an eleventh aspect, colors of the two forming materials of the hardness-transition section are different from each other.

In the microcatheter according to a twelfth aspect, the outer layer has the hardness-transition section between a distal section of the distal tip side and a proximal section of the proximal end side.

In the microcatheter according to a thirteenth aspect, the outer layer has the hardness-transition section between the distal section of the distal tip side and the proximal section of the proximal end side, the distal section includes the first forming material extending from the hardness-transition section, and the proximal section includes the second forming material extending from the hardness-transition section.

In the microcatheter according to a fourteenth aspect, length of the hardness-transition section is 150 mm to 400 mm of the length of the outer layer.

Advantageous Effects of Invention

According to the present disclosure, due to having, in the entire or partial lengthwise direction length of the outer layer, the hardness-transition section in which hardness of the outer layer increases along the lengthwise direction from the distal tip to the proximal tip, in addition to an ability to improve operability, in particular the second forming material is arranged in a stripe pattern extending in the lengthwise direction of the outer layer, and thus transmission of force is enabled that differs with the circumferential direction position rather than the conventional propagation of uniform force, and operability is further improved by enablement of operation with distal tip directionality.

DESCRIPTION OF EMBODIMENTS

Figure 1:
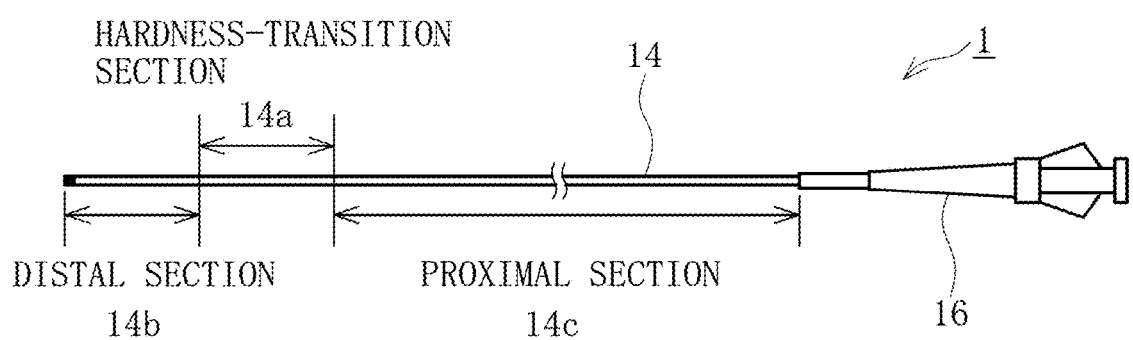
FIG. 1 is a descriptive drawing illustrating an example of external appearance of a microcatheter according to the present disclosure.
Figure 2:
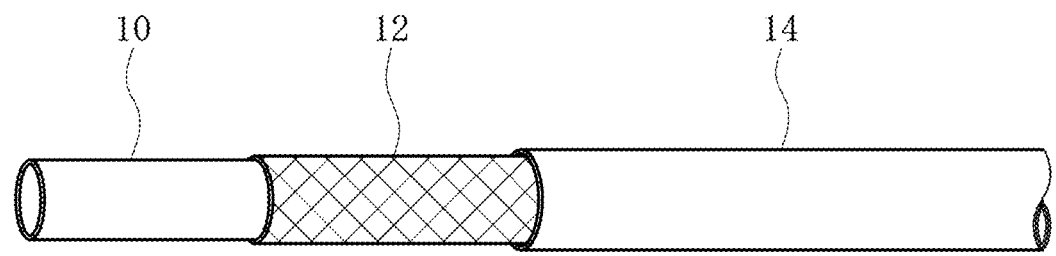
FIG. 2 is a descriptive drawing illustrating an example of internal structure of the same microcatheter.

A microcatheter according to the present disclosure is a catheter that is inserted into a narrow blood vessel for treatment or diagnosis of an organ or a blood vessel. FIG. 1 is a descriptive drawing illustrating an example of external appearance of the microcatheter according to the present disclosure, and FIG. 2 is a descriptive drawing illustrating an example of internal structure of the same microcatheter. As illustrated in FIG. 2, a microcatheter 1 includes an inner layer 10 along the entire length, a reinforcing layer 12 that reinforces the inner layer 10, and an outer layer 14 serving as an outer wall layer.

Due to the inner layer 10 being a long tubular body formed from a fluorocarbon resin, for example, the microcatheter 1 achieves excellent sliding in the inner cavity. High anti-kinking performance is achieved by the reinforcing layer 12 covered by the inner layer 10 in order to protect the inner layer 10, and for example, forming the reinforcing layer 12 from a fine nylon mesh.

As illustrated in FIG. 1, the outer layer 14 of the microcatheter 1 has a hardness-transition section 14a between a distal section 14b of the distal tip side and a proximal section 14c of the proximal end side. The hardness-transition section 14a is a part in which hardness of the outer layer 14 varies so as to increase along the lengthwise direction from the distal tip to the proximal tip, and is arranged in portion of the length of the outer layer 14. In this case, the length of the hardness-transition section 14a, is preferably 150 mm to 400 mm of the length of the outer layer 14 in a general microcatheter that, for example, has a distal section 14b of about 150 mm and a proximal section 14c of about 150 mm to 800 mm. In addition to the case in which the hardness-transition section 14 is arranged in part of the microcatheter 1, the hardness-transition section 14a may be arranged in the entire outer layer 14, or the hardness-transition section 14a may be arranged at a number of locations.

In the hardness-transition section 14a of the microcatheter 1 according to the present disclosure, hardness of the outer layer 14 varies so as to increase along the lengthwise direction from the distal tip to the proximal tip due to arrangement of a second forming material in a stripe pattern extending in the lengthwise direction of the outer layer 14 in the first forming material including a forming material capable of forming the outer layer 14, and varying in the lengthwise direction a surface area ratio of the first forming material and the second forming material in the circumferential direction cross section of the two forming materials, the two materials being the first forming material and the second forming material. Further, the surface area ratio of the two forming materials of the hardness-transition section 14*a* varies in a stepwise or linear manner along the lengthwise direction. The second forming material of the hardness-transition section 14*a* is not limited to a linear stripe shape, and, for example, may be sinuous in the lengthwise direction rather than linear.

The first forming material and the second forming material may be any materials capable of forming the outer layer 14, such as resin materials. Specific examples of resin materials capable of being used as the forming materials include: polyamides such as polyamide elastomers, nylon, and the like; olefins such as polypropylene, polyethylene, and the like; polyesters such as polyester elastomers, polyethylene terephthalate, and the like; as well as polyurethanes and the like; although thermoplastic resins are preferred, the resins are not limited to thermoplastic resins.

Hardness values of the two forming materials of the hardness-transition section 14*a* are preferably such that one forming material has a Shore hardness of 20 D to 30 D, and the other forming material has a shore hardness of 65 D to 80 D. Shore hardness is determined in accordance with ISO 868. Further, the hardness values of the two forming materials of the hardness-transition section 14*a* are preferably set such that the hardness values of the two forming materials of the hardness-transition section 14*a* have a ½-fold to ¼-fold difference. Colors of the two forming materials of the hardness-transition section 14*a* may be different.

The type of variation in the surface area ratio of the two forming materials of the hardness-transition section 14*a* may be freely selected, such as partial stepwise variation and partial linear variation, and the like. Although the first forming material and the second forming material of the hardness-transition section 14*a* in the present disclosure are described as each being a single type of material, for example, the first forming material may be formed from multiple types of materials, each or some of the multiple stripes of the second forming material may be formed from multiple types of materials, such as materials of different hardness values, without particular limitation.

Further, multiple modes are conceivable as modes of variation in the lengthwise direction of the surface area ratio of the first forming material and the second forming material in the circumferential direction cross section of the two forming materials of the hardness-transition section 14*a* of the outer layer 14. For example, a mode exists in which the surface area ratio of the two forming materials varies along the lengthwise direction by causing lengthwise direction variation in the surface area in the circumferential direction occupied by the second forming material relative to the first forming material of the hardness-transition section 14*a*.

Further, as a mode of variation along the lengthwise direction of the surface area ratio of the two forming materials in the circumferential direction cross section for the first forming material and the second forming material of the hardness-transition section 14*a* of the outer layer 14, a mode also exists in which the surface area ratio of the two forming materials varies in the lengthwise direction by causing lengthwise direction variation in the surface area in the thickness direction occupied by the second forming material relative to the first forming material of the hardness-transition section 14*a*.

Further, as a mode of variation along the lengthwise direction of the surface area ratio of the two forming materials in the circumferential direction cross section for the first forming material and the second forming material of the hardness-transition section 14*a* of the outer layer 14, a mode also exists in which the surface area ratio of the two forming materials is made to vary along the lengthwise direction in surface area in the circumferential direction and the thickness direction occupied by the second forming material relative to the first forming material of the hardness-transition section 14*a*. In this manner, multiple modes can exist for the variation in the lengthwise direction for the surface area ratio of the two forming materials occupied in the circumferential direction cross section for the first forming material and the second forming material of the outer layer 14, although the aforementioned modes are not limiting.

The microcatheter 1 configured in this manner has the hardness-transition section 14*a*, in which hardness of the outer layer 14 varies so as to increase from the distal tip to the proximal tip along the lengthwise direction, that is the entire or partial length of the outer layer 14, and thus operability can be improved, and particularly the second forming material is arranged in a stripe pattern extending in the lengthwise direction of the outer layer 14, thereby enabling transmission of force that differs with circumferential direction position rather than force propagating uniformly in the conventional manner, enabling operation with good directionality of the distal tip, and further improving operability.

The description of the present embodiment is merely a preferred embodiment of the present disclosure, the technical scope of the present disclosure, as long as within the scope of the gist of the present disclosure, is not limited to the scope described in each of the embodiments. Specific details of the hardness-transition section are illustrated by using the below examples.

Embodiment 1

Figure 3:
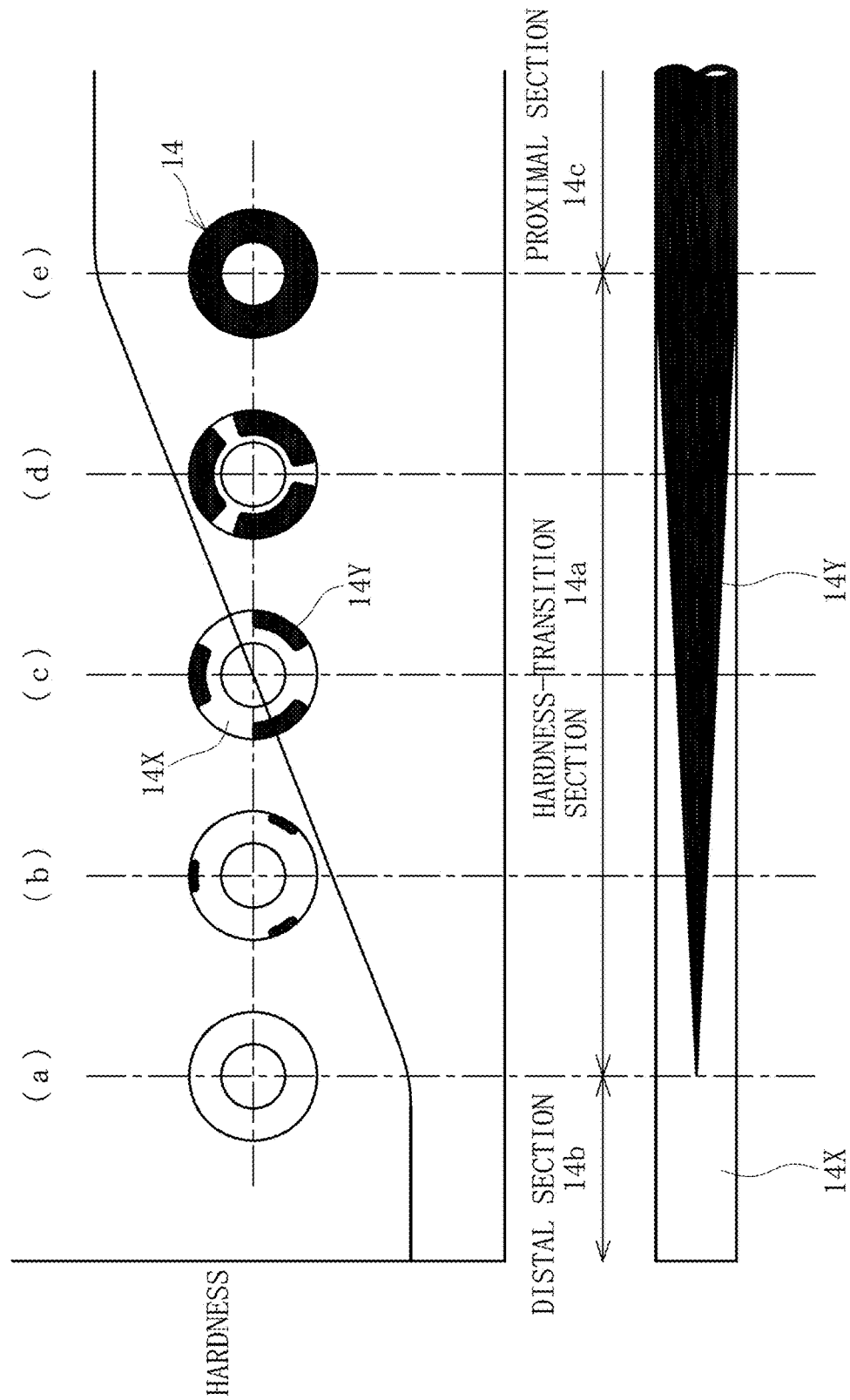
FIG. 3 is a descriptive drawing illustrating an example of structure of a microcatheter according to Embodiment 1 of the present disclosure.

A detailed example of the hardness-transition section 14*a* of the outer layer 14 of the microcatheter 1 of Embodiment 1 is described below. Although configurations of hardness-transition sections of other outer layers are described in the below descriptions of other embodiments, the basic structure of the microcatheter is the same as illustrated in FIGS. 1 and 2, and thus the microcatheter 1 is described, and descriptions of parts other than the hardness-transition section are basically omitted. FIG. 3 is a descriptive drawing illustrating an example of structure of the microcatheter according to Embodiment 1 in the present disclosure.

In the outer layer 14 of the microcatheter 1 of Embodiment 1, the surface area ratio of two forming materials 14X and 14Y varies in the lengthwise direction due to varying in the lengthwise direction the surface areas in the circumferential direction and thickness direction occupied by the forming material 14Y that is the second forming material, relative to the forming material 14X that is the first forming material of the hardness-transition section 14*a*. Further, due to varying along the lengthwise direction of the surface area ratio of the two forming materials 14X and 14Y of the hardness-transition section 14*a*, as illustrated in the graph of hardness in FIG. 3, the hardness of the outer layer 14 varies so as to increase along the lengthwise direction from the distal tip to the proximal tip.

More specifically, the forming material 14Y is formed from three stripes arranged in the circumferential direction, and by variation along the lengthwise direction of the surface area in the circumferential direction and thickness direction occupied by the forming material 14Y relative to the forming material 14X, the surface area ratio of the two forming materials 14X and 14Y varies along the lengthwise direction. As illustrated in FIG. 3, in a cross section "a" nearest the vicinity of the distal tip, the entire cross sectional area is occupied by the forming material 14X. In a cross section "b" near the proximal tip, the forming material 14Y appears in a portion of the outer circumference, and as the proximal tip is further approached as illustrated in the cross section "c" and the cross section "d", the surface area of the forming material 14Y increases in the circumferential direction and the thickness direction. Then at the proximal end side tip of the hardness-transition section 14a, as illustrated in the cross section "e", the cross sectional is made of only the forming material 14Y.

The forming material 14X is a material having a Shore hardness in the range of 20 D to 30 D, and specifically about 26 D; and the forming material 14Y is a material having a Shore hardness in the range of 65 D to 80 D, and specifically about 73 D.

The distal section 14b of the outer layer 14 is formed from the forming material 14X that is the first forming material extending from the hardness-transition section 14a; and the proximal section 14c is formed from the forming material 14Y that is the second forming material extending from the hardness-transition section 14a. That is, the distal section 14b is made of a substance that is softer than the substance of the proximal section 14c.

Figure 4:
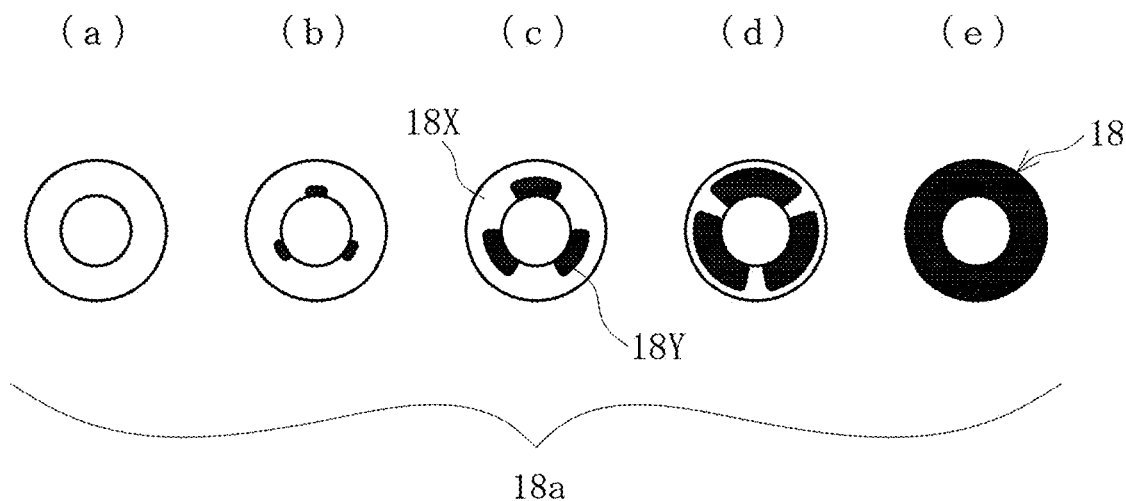
FIG. 4 is a descriptive drawing illustrating another example of structure of the microcatheter according to Embodiment 1 of the present disclosure.

Although the high-hardness forming material 14Y is arranged at the outer circumferential side in the hardness-transition section 14a as illustrated in FIG. 3, this configuration is not limiting, and arrangement is possible at the inner circumferential side as in the FIG. 4, a descriptive drawing illustrating another example of structure of the microcatheter according to Embodiment 1 of the present disclosure. In a hardness-transition section 18a of the outer layer 18 in the example illustrated in FIG. 4, the forming material 18Y that is the second forming material is arranged at the inner circumferential side relative to the forming material 18X that is the first forming material. More specifically, as illustrated in FIG. 4, in a cross section "b" approaching the proximal tip, the forming material 18Y appears in a portion of the inner circumference, and as the proximal tip is further approached as illustrated in the cross section "c" and the cross section "d", the surface area of the forming material 18Y increases in the circumferential direction and the thickness direction. Then at the proximal end side tip of the hardness-transition section 18a, as illustrated in the cross section "e", the cross sectional is made of only the forming material 18Y.

Embodiment 2

Figure 5:
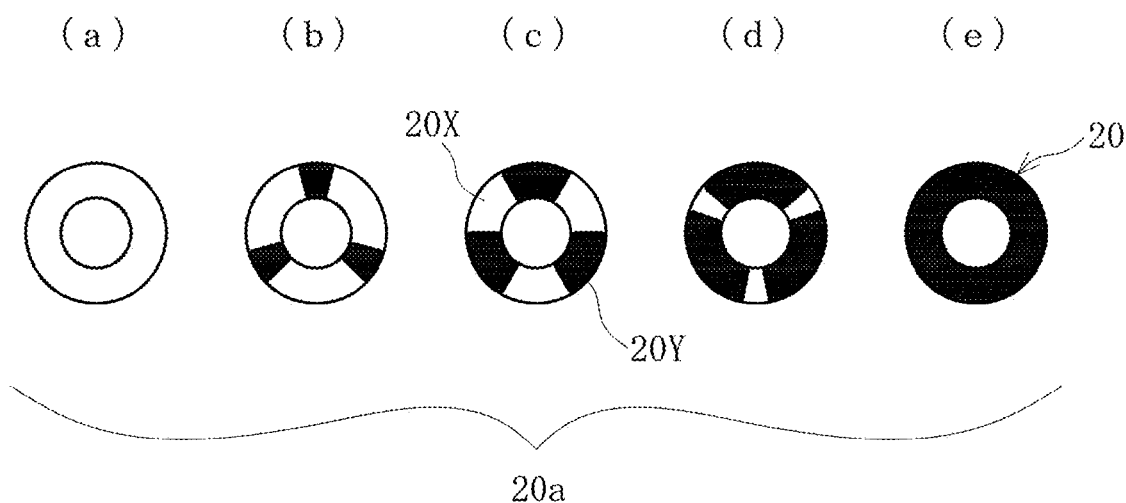
FIG. 5 is a descriptive drawing illustrating an example of structure of a microcatheter according to Embodiment 2 of the present disclosure.

A detailed example of a hardness-transition section 20a of an outer layer 20 of a microcatheter 1 of Embodiment 2 is described below. FIG. 5 is a descriptive drawing illustrating an example of structure of the microcatheter according to Embodiment 2 in the present disclosure.

In the outer layer 20 of the microcatheter 1 of Embodiment 2, the surface area ratio of two forming materials 20X and 20Y varies in the lengthwise direction due to varying in the lengthwise direction the surface area in the circumferential direction occupied by the forming material 20Y that is the second forming material, relative to the forming material 20X that is the first forming material of a hardness-transition section 20a. Further, due to varying along the lengthwise direction of the surface area ratio of the two forming materials 20X and 20Y of the hardness-transition section 20a, the hardness of the outer layer 20 varies so as to increase along the lengthwise direction from the distal tip to the proximal tip.

More specifically, the forming material 20Y is formed from three stripes arranged in the circumferential direction, and by variation along the lengthwise direction of the surface area in the circumferential direction occupied by the forming material 20Y relative to the forming material 20X, the surface area ratio of the two forming materials 20X and 20Y varies along the lengthwise direction. As illustrated in FIG. 5 in a cross section "a" nearest the vicinity of the distal tip, the entire cross sectional area is occupied by the forming material 20X. In a cross section "b" approaching the proximal tip, the forming material 20Y appears in a portion in the outward direction, and as the proximal tip is further approached as illustrated in the cross section "c" and the cross section "d", the surface area of the forming material 20Y increases in the circumferential direction. Then at the proximal end side tip of the hardness-transition section 20a, as illustrated in the cross section "e", the cross sectional is made of only the forming material 20Y.

The forming material 20X is a material having a Shore hardness in the range of 20 D to 30 D, and specifically about 26 D; and the forming material 20Y is a material having a Shore hardness in the range of 65 D to 80 D, and specifically about 73 D.

Embodiment 3

Figure 6:
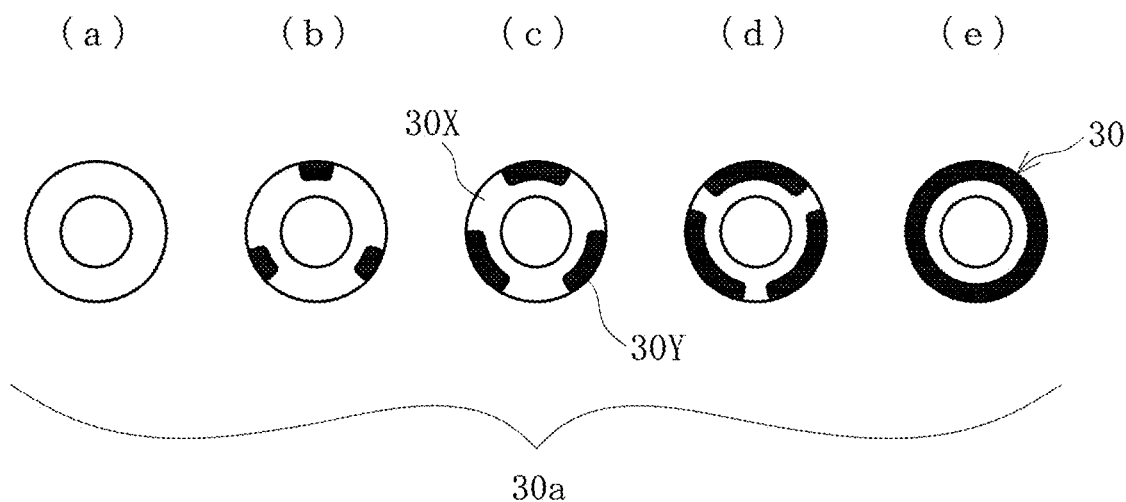
FIG. 6 is a descriptive drawing illustrating an example of structure of a microcatheter according to Embodiment 3 of the present disclosure.

A detailed example of a hardness-transition section 30a of an outer layer 30 of the microcatheter 1 of Embodiment 3 is described below. FIG. 6 is a descriptive drawing illustrating an example of structure of the microcatheter according to Embodiment 3 in the present disclosure.

In the outer layer 30 of the microcatheter 1 of Embodiment 3, the surface area ratio of two forming materials 30X and 30Y varies in the lengthwise direction due to varying in the lengthwise direction the surface area in the circumferential direction occupied by the forming material 30Y that is the second forming material, relative to the forming material 30X that is the first forming material of a hardness-transition section 30a. Further, due to varying along the lengthwise direction of the surface area ratio of the two forming materials 30X and 30Y of the hardness-transition section 30a, the hardness of the outer layer 30 varies so as to increase along the lengthwise direction from the distal tip to the proximal tip.

More specifically, the forming material 30Y is formed from three stripes arranged in the circumferential direction, and by variation along the lengthwise direction of the surface area in the circumferential direction occupied by the forming material 30Y relative to the forming material 30X, the surface area ratio of the two forming materials 30X and 30Y varies along the lengthwise direction. As illustrated in FIG. 6 in a cross section "a" in the nearest vicinity to the distal tip, the entire cross sectional area is occupied by the forming material 30X. In a cross section "b" approaching the proximal tip, the forming material 30Y appears in a portion of the outer circumference, and as the proximal tip is further approached as illustrated in the cross section "c" and the cross section "d", the surface area of the forming material 30Y increases in the circumferential direction. Then at the proximal end side tip of the hardness-transition section 30a, as illustrated in the cross section "e", the cross sectional is made of only the forming material 30Y.

The forming material 30X is a material having a Shore hardness in the range of 20 D to 30 D, and specifically about 26 D; and the forming material 30Y is a material having a Shore hardness in the range of 65 D to 80 D, and specifically about 73 D.

Figure 7:
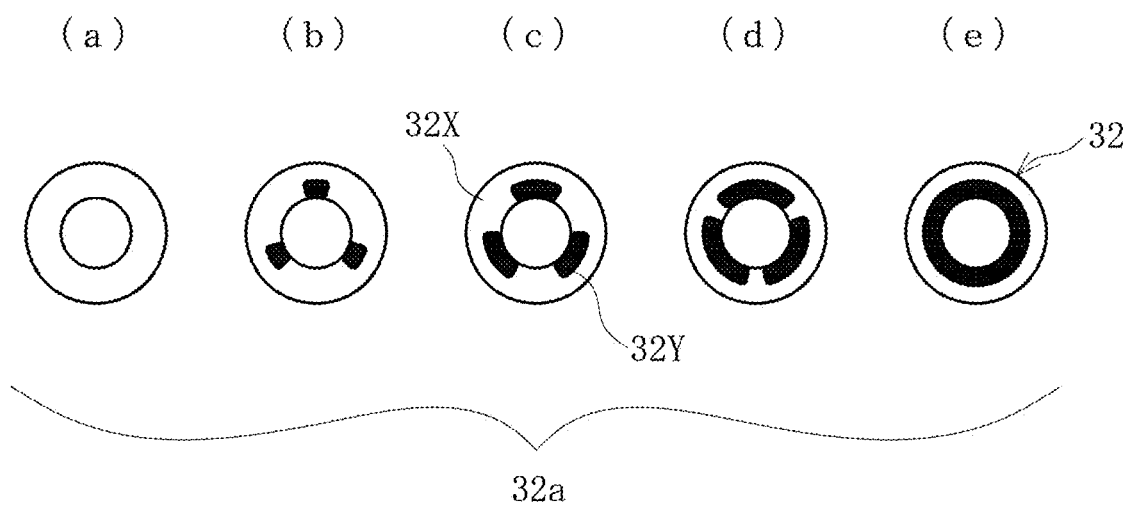
FIG. 7 is a descriptive drawing illustrating another example of structure of the microcatheter according to Embodiment 3 of the present disclosure.

Although the high-hardness forming material 30Y is arranged at the outer circumferential side in the hardness-transition section 30a as illustrated in FIG. 6, this configuration is not limiting, and arrangement is possible at the inner circumferential side as in the FIG. 7, a descriptive drawing illustrating another example of structure of the microcatheter according to Embodiment 3 of the present disclosure. In a hardness-transition section 32a of the outer layer 32 in the example illustrated in FIG. 7, the forming material 32Y that is the second forming material is arranged at the inner circumferential side relative to the forming material 32X that is the first forming material. More specifically, as illustrated in FIG. 7, in a cross section "b" approaching the proximal tip, the forming material 32Y appears in a portion of the inner circumference, and as the proximal tip is further approached as illustrated in the cross section "c" and the cross section "d", the surface area of the forming material 32Y increases in the circumferential direction. Then at the proximal end side tip of the hardness-transition section 32a, as illustrated in the cross section "e", the cross sectional is made of only the forming material 32Y.

Embodiment 4

Figure 8:
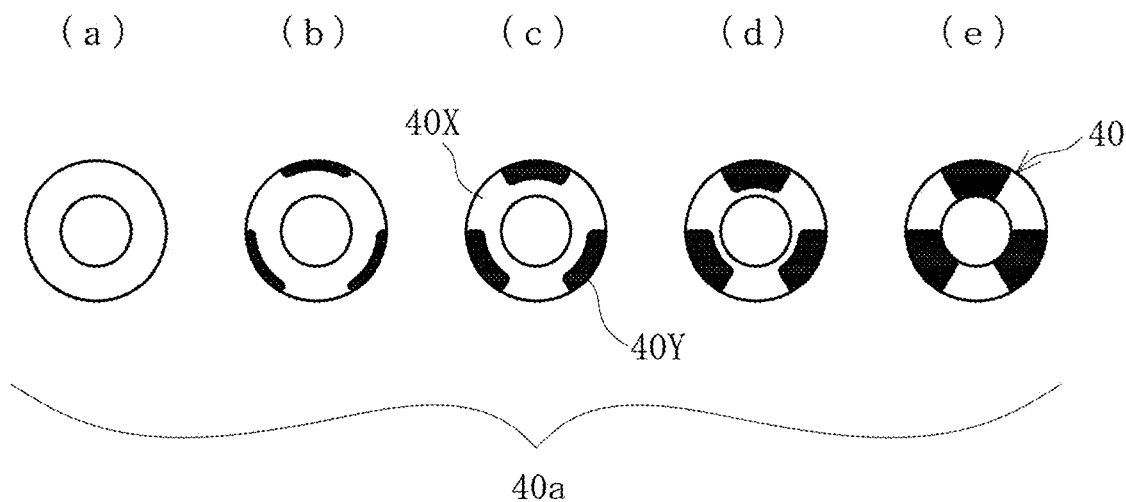
FIG. 8 is a descriptive drawing illustrating an example of structure of a microcatheter according to Embodiment 4 of the present disclosure.

A detailed example of a hardness-transition section 30a of an outer layer 30 of the microcatheter 1 of Embodiment 4 is described below. FIG. 8 is a descriptive drawing illustrating an example of structure of the microcatheter according to Embodiment 4 in the present disclosure.

In the outer layer 40 of the microcatheter 1 of Embodiment 4, the surface area ratio of two forming materials 40X and 40Y varies in the lengthwise direction due to varying in the lengthwise direction of the surface area in the thickness direction occupied by the forming material 40Y that is the second forming material, relative to the forming material 40X that is the first forming material of a hardness-transition section 40a. Further, due to varying along the lengthwise direction of the surface area ratio of the two forming materials 40X and 40Y of the hardness-transition section 40a, the hardness of the outer layer 40 varies so as to increase along the lengthwise direction from the distal tip to the proximal tip.

More specifically, the forming material 40Y is formed from three stripes arranged in the circumferential direction, and by variation along the lengthwise direction of the surface area in the thickness direction occupied by the forming material 40Y relative to the forming material 40X, the surface area ratio of the two forming materials 40X and 40Y varies along the lengthwise direction. As illustrated in FIG. 8 in a cross section "a" in the nearest vicinity to the distal tip, the entire cross sectional area is occupied by the forming material 40X. In a cross section "b" approaching the proximal tip, the forming material 40Y appears in a certain portion of the outer circumference, and as the proximal tip is further approached as illustrated in the cross section "c" and the cross section "d", the surface area of the forming material 40Y increases in the thickness direction. Then at the proximal end side tip of the hardness-transition section 40a, as illustrated in the cross section "e", the forming material 40Y reaches the inner circumference.

The forming material 40X is a material having a Shore hardness in the range of 20 D to 30 D, and specifically about 26 D; and the forming material 40Y is a material having a Shore hardness in the range of 65 D to 80 D, and specifically about 73 D.

Figure 9:
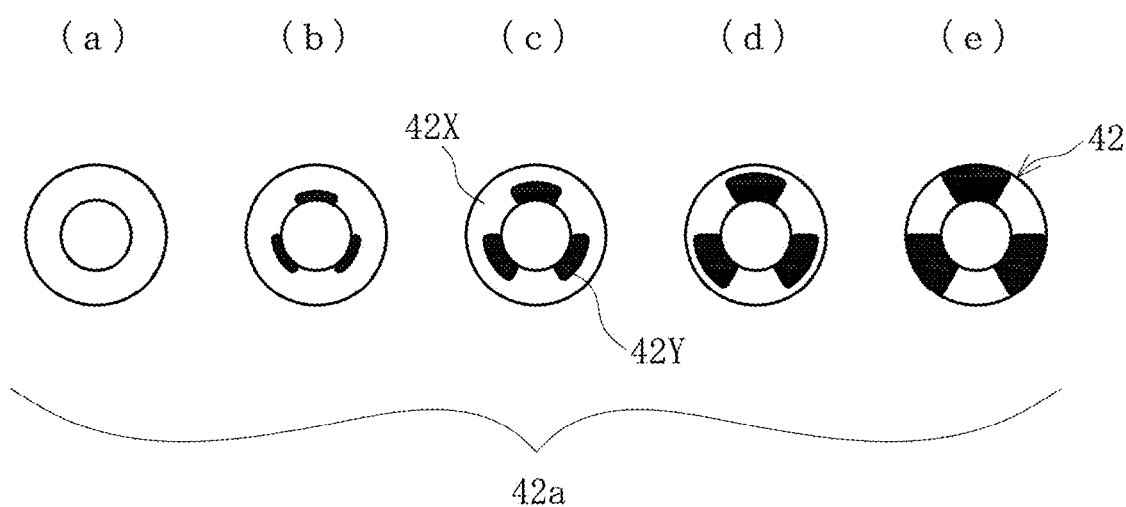
FIG. 9 is a descriptive drawing illustrating another example of structure of the microcatheter according to Embodiment 4 of the present disclosure.

Although the high-hardness forming material 40Y is arranged at the outer circumferential side in the hardness-transition section 40a as illustrated in FIG. 8, this configuration is not limiting, and arrangement is possible at the inner circumferential side as in the FIG. 9, a descriptive drawing illustrating another example of structure of the microcatheter according to Embodiment 4 of the present disclosure. In a hardness-transition section 42a of the outer layer 42 in the example illustrated in FIG. 9, the forming material 42Y that is the second forming material is arranged at the inner circumferential side relative to the forming material 42X that is the first forming material. More specifically, as illustrated in FIG. 9, in a cross section "b" approaching the proximal tip, the forming material 42Y appears in a certain portion of the inner circumference, and as the proximal tip is further approached as illustrated in the cross section "c" and the cross section "d", the surface area of the forming material 42Y increases in the thickness direction. Then at the proximal end side tip of the hardness-transition section 42a, as illustrated in the cross section "e", the forming material 42Y reaches the outer circumference.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

This application claims the benefit of Japanese Patent Application No. 2016-094310, filed on May 10, 2016, the entire disclosure of which is incorporated by reference herein.

INDUSTRIAL APPLICABILITY

In accordance with the present disclosure as described above, a microcatheter can be provided that enables improvement of operability, enables transmission of force that differs with position along the circumferential direction rather than the conventional propagation of uniform force, enables operation of the distal tip with good directionality, and further improves operability.

REFERENCE SIGNS LIST

1 Microcatheter
10 Inner layer
12 Reinforcing layer
14 Outer layer
14a Hardness-transition section
14b Distal section
14c Proximal section
14X Forming material
14Y Forming material 16 Operating section
18 Outer layer
18a Hardness-transition section
18X Forming material
18Y Forming material
20 Outer layer
20a Hardness-transition section
20X Forming material
20Y Forming material
30 Outer layer
30a Hardness-transition section
30X Forming material
30Y Forming material
32 Outer layer
32a Hardness-transition section
32X Forming material
32Y Forming material
40 Outer layer
40a Hardness-transition section
40X Forming material
40Y Forming material
42 Outer layer
42a Hardness-transition section
42X Forming material
42Y Forming material

What is claimed is:

1. A microcatheter comprising:
an inner layer along an entire length of the microcatheter;
a reinforcing layer that reinforces the inner layer;
an outer layer serving as an outer wall layer; and
a hardness-transition section in a part or an entire lengthwise direction length of the outer layer, wherein
by arrangement of a second forming material in a three striped pattern extending in the lengthwise direction of the outer layer in a first forming material included in forming materials formable into the outer layer, and by varying along the lengthwise direction of a surface area ratio of the two forming materials occupied in a cross section in a circumferential direction between the first forming material and the second forming material, hardness of the outer layer varies so as to increase from a distal tip to a proximal tip along the lengthwise direction.

2. A microcatheter comprising:
an inner layer along an entire length of the microcatheter;
a reinforcing layer that reinforces the inner layer;
an outer layer serving as an outer wall layer; and
a hardness-transition section in a part or an entire lengthwise direction length of the outer layer, wherein
by arrangement of a second forming material in a three striped pattern extending in the lengthwise direction of the outer layer in a first forming material included in forming materials formable into the outer layer, and by varying along the lengthwise direction of a surface area ratio of the two forming materials occupied in a cross section in a circumferential direction between the first forming material and the second forming material, hardness of the outer layer varies so as to increase from a distal tip to a proximal tip along the lengthwise direction, and
the surface area ratio of the two forming materials of the hardness-transition section varies in a stepwise or linear manner along the lengthwise direction.

3. The microcatheter according to claim 1, wherein, by lengthwise-direction variation of the surface area ratio of the surface area occupied in the circumferential direction by the second forming material relative to the first forming material in the hardness-transition section, a surface area ratio of the two forming materials varies along the lengthwise direction.

4. The microcatheter according to claim 1, wherein
the second forming material of the hardness-transition section includes three stripes arranged in the circumferential direction, and
by lengthwise-direction variation of the surface area ratio of the surface area occupied in the circumferential direction by the second forming material relative to the first forming material in the hardness-transition section, a surface area ratio of the two forming materials varies along the lengthwise direction.

5. The microcatheter according to claim 1, wherein
the surface area ratio of the two forming materials varies along the lengthwise direction due to varying along the lengthwise direction of a surface area in a thickness direction occupied by the second forming material relative to the first forming material of the hardness-transition section.

6. The microcatheter according to claim 1, wherein
the second forming material of the hardness-transition section includes three stripes arranged in the circumferential direction, and
the surface area ratio of the two forming materials varies along the lengthwise direction due to varying along the lengthwise direction of a surface area in a thickness direction occupied by the second forming material relative to the first forming material.

7. The microcatheter according to claim 1, wherein the surface area ratio of the two forming materials varies along the lengthwise direction due to varying along the lengthwise direction of a surface area in the circumferential direction and a thickness direction occupied by the second forming material relative to the first forming material of the hardness-transition section.

8. The microcatheter according to claim 1, wherein
the second forming material of the hardness-transition section includes three stripes arranged in the circumferential direction, and
the surface area ratio of the two forming materials varies along the lengthwise direction due to varying along the lengthwise direction of a surface area in the circumferential direction and a thickness direction occupied by the second forming material relative to the first forming material.

9. The microcatheter according to claim 1, wherein, among the two forming materials of the hardness-transition section, Shore hardness of one forming material is 20 D to 30 D, and Shore hardness of the other forming material is 65 D to 80 D.

10. The microcatheter according to claim 1, wherein hardness values of the two forming materials of the hardness-transition section have a ½-fold to ¼-fold difference.

11. The microcatheter according to claim 1, wherein colors of the two forming materials of the hardness-transition section are different from each other.

12. The microcatheter according to claim 1, wherein the outer layer comprises the hardness-transition section between a distal section at a distal tip side and a proximal section at a proximal end side.

13. The microcatheter according to claim 1, wherein
the outer layer comprises the hardness-transition section between a distal section of a distal tip side and a proximal section of a proximal end side,
the distal section comprises the first forming material extending from the hardness-transition section, and the proximal section comprises the second forming material extending from the hardness-transition section.

14. The microcatheter according to claim 1, wherein a length of the hardness-transition section is 150 mm to 400 mm of a length of the outer layer.

15. The microcatheter according to claim 2, wherein, by lengthwise-direction variation of the surface area ratio of the surface area occupied in the circumferential direction by the second forming material relative to the first forming material in the hardness-transition section, a surface area ratio of the two forming materials varies along the lengthwise direction.

16. The microcatheter according to claim 2, wherein
the second forming material of the hardness-transition section includes three stripes arranged in the circumferential direction, and
by lengthwise-direction variation of the surface area ratio of the surface area occupied in the circumferential direction by the second forming material relative to the first forming material in the hardness-transition section, a surface area ratio of the two forming materials varies along the lengthwise direction.

17. The microcatheter according to claim 2, wherein
the surface area ratio of the two forming materials varies along the lengthwise direction due to varying along the lengthwise direction of a surface area in a thickness direction occupied by the second forming material relative to the first forming material of the hardness-transition section.

18. The microcatheter according to claim 2, wherein
the second forming material of the hardness-transition section includes three stripes arranged in the circumferential direction, and
the surface area ratio of the two forming materials varies along the lengthwise direction due to varying along the lengthwise direction of a surface area in a thickness direction occupied by the second forming material relative to the first forming material.

19. The microcatheter according to claim 2, wherein the surface area ratio of the two forming materials varies along the lengthwise direction due to varying along the lengthwise direction of a surface area in the circumferential direction and a thickness direction occupied by the second forming material relative to the first forming material of the hardness-transition section.

20. The microcatheter according to claim 2, wherein
the second forming material of the hardness-transition section includes three stripes arranged in the circumferential direction, and
the surface area ratio of the two forming materials varies along the lengthwise direction due to varying along the lengthwise direction of a surface area in the circumferential direction and a thickness direction occupied by the second forming material relative to the first forming material.

* * * * *